United States Patent
Guieze et al.

[11] Patent Number: 6,041,668
[45] Date of Patent: Mar. 28, 2000

[54] METHOD AND APPARATUS FOR TAKING SAMPLES IN A GAS OUTLET PIPE OF A LIQUID/GAS SEPARATOR FED WITH AN OIL WELL EFFLUENT

[75] Inventors: Paul B. Guieze, Fontenailles; Pierre F. Le Foll, Antony, both of France

[73] Assignee: Schlumberger Technology Corporation, Houston, Tex.

[21] Appl. No.: 09/201,360

[22] Filed: Nov. 30, 1998

[30] Foreign Application Priority Data

May 12, 1997 [FR] France .................................. 97 15385

[51] Int. Cl.[7] .................................................... G01N 1/00
[52] U.S. Cl. ............................................................ 73/863.03
[58] Field of Search ........................... 73/863.03, 863.11, 73/863.12, 863.81; 55/410, 417, 423

[56] References Cited

U.S. PATENT DOCUMENTS

| | | |
|---|---|---|
| 3,921,458 | 11/1975 | Logan . |
| 5,211,842 | 5/1993 | Tuss et al. ............................. 73/863.03 |
| 5,369,981 | 12/1994 | Merz et al. . |
| 5,408,868 | 4/1995 | Ortega et al. . |
| 5,456,124 | 10/1995 | Colvin ................................... 73/863.11 |

FOREIGN PATENT DOCUMENTS

| | | |
|---|---|---|
| 2198805 | 9/1997 | Canada . |
| 0 791 421 | 9/1997 | European Pat. Off. . |
| WO 95/18366 | 7/1995 | WIPO . |
| WO 98/33051 | 7/1998 | WIPO . |

*Primary Examiner*—Robert Raevis
*Attorney, Agent, or Firm*—John J. Ryberg; Brigitte L. Jeffery

[57] ABSTRACT

A sample of fluid such as a gaseous fluid leaving a liquid/gas separator in a surface installation of an oil well, is taken continuously via a sampling tube. The tube opens out on the axis of a gas outlet pipe, facing towards the separator receptacle and located at the junction between the pipe and the receptacle. Sampling is performed isokinetically by regulating the flow rate in the tube by means of a regulator valve controlled by a regulator as a function of flow rates measured in the tube and in the pipe. In the tube, liquid is separated from the gas by means of a filter.

16 Claims, 1 Drawing Sheet

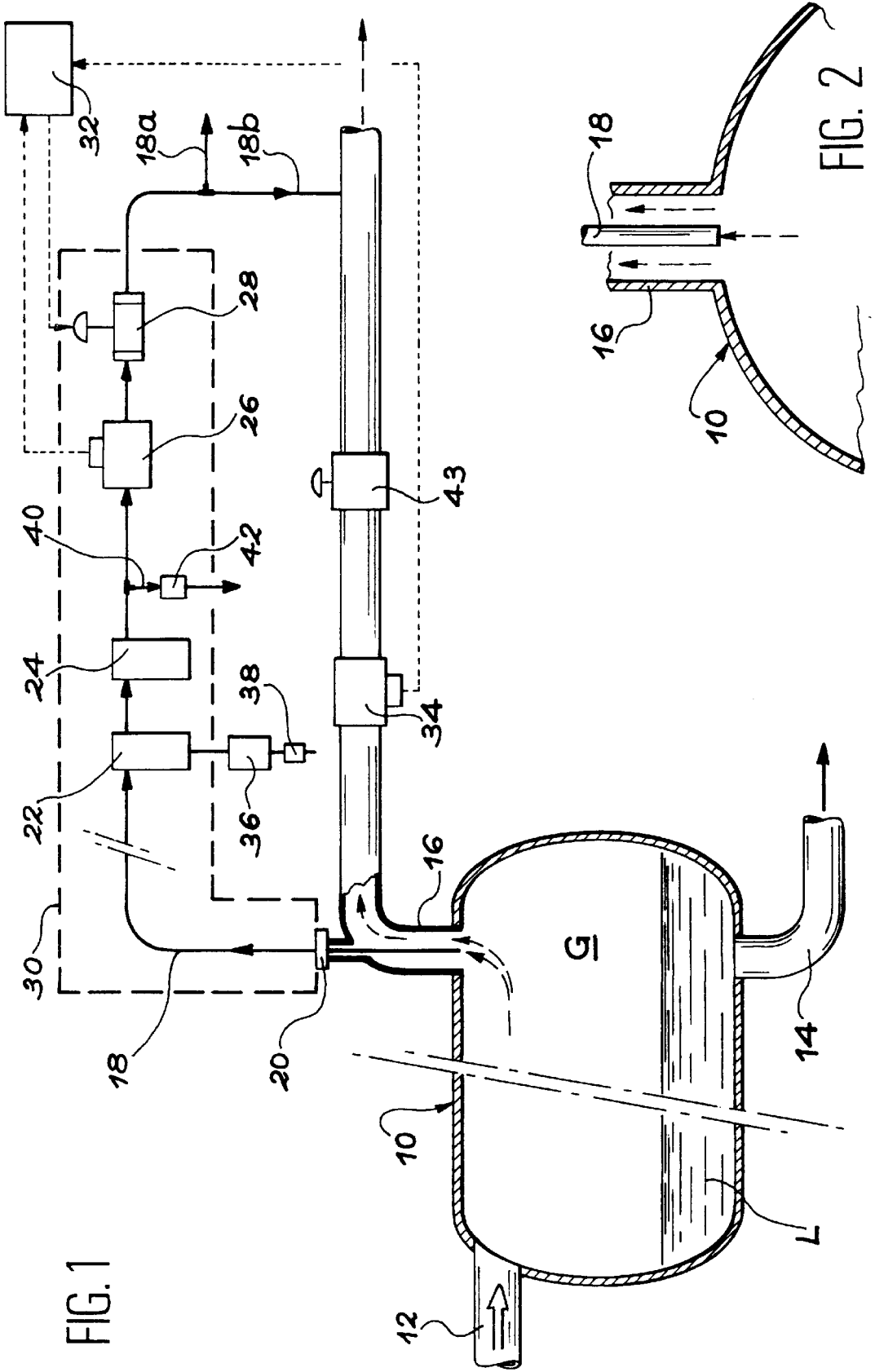

METHOD AND APPARATUS FOR TAKING SAMPLES IN A GAS OUTLET PIPE OF A LIQUID/GAS SEPARATOR FED WITH AN OIL WELL EFFLUENT

TECHNICAL FIELD

The invention relates to a method of taking samples in a gas outlet pipe of a liquid/gas separator fed with an oil well effluent.

The invention also relates to apparatus enabling the method to be implemented.

The method and the apparatus of the invention for taking samples are useful in surface installations fitted to oil wells during testing prior to operating the wells, for the purpose of determining the characteristics of the petroleum fluid coming from the wells. In particular, the method and apparatus of the invention are particularly adapted to the case where the petroleum fluid flowing from the well has a very high gas content.

STATE OF THE ART

The purpose of oil well test installations is to determine as accurately as possible the characteristics of the petroleum fluid contained in the underground reservoir to which the well gives access. These characteristics include, in particular, the nature and proportions of the various phases making up the petroleum fluid.

For that purpose, existing installations usually comprise means for separating the various phases of the fluid and means for taking samples of the petroleum fluid. The design and organization of those various means differ depending on the installation.

Thus, in document U.S. Pat. No. 4,301,679, samples are taken intermittently, by taking off petroleum fluid at well pressure via a pipe into which a sampling tube opens out. The end of the sampling tube is placed in the center of a constriction formed in the pipe, downstream from fluid mixing means constituted by some number of convergent channels machined in a part that is placed in the pipe at the inlet to the constriction. More precisely, the end of the sampling tube is placed at the point where the channels converge. The end of the sampling tube may face either radially or along the axis of the constriction. The fluid taken by the tube is then conveyed, for example, to a liquid gas separator from which samples can be taken in evacuated receptacles.

In that known installation, the purpose of passing the petroleum fluid through the mixing means is to ensure that the sample taken is as representative as possible of the fluid flowing in the pipe. In practice, the representativeness of the sample is nevertheless uncertain.

If the liquid and gas phases are separated downstream from the sampling point, then droplets of liquid in suspension can be entrained in the gas phase leaving the separator. When the petroleum fluid whose characteristics are to be discovered has a very high gas content, these droplets of liquid entrained by the gas phase can represent a significant fraction of the liquid actually present in the petroleum fluid. Consequently, a measurement of the liquid and gaseous fractions of the fluid performed on the basis of the quantities of fluid flowing via the liquid and gas outlet pipes of the separator then provide information that is erroneous. More precisely, measurements performed in that way depart increasingly from reality with decreasing content of liquid in the petroleum fluid.

In addition, it can turn out that the liquid entrained by the gas at the outlet from the separator is partially or totally different from the liquid collected via the liquid outlet pipe of the separator. Unfortunately, there is no way at present of knowing the nature of the liquid that has been entrained by the gas.

In other existing installations, all of the petroleum fluid coming from the well passes through a liquid/gas separator and samples of liquid and of gas are collected downstream from the separator, respectively from its liquid and gas outlet pipes.

In those installations, the main problems mentioned above with reference to document U.S. Pat. No. 4,301,679 also apply.

In document WO-A-93/02345, a device is proposed for taking spot samples of a fluid flowing under high pressure in any component, such as a separator or a duct. The device comprises two concentric sampling tubes that are movable in a direction that is perpendicular to the fluid flow. Thus, a sampling endpiece mounted at the end of the tubes can be moved between a central region of the component and a region situated close to a wall, thereby enabling fluid samples to be taken from different locations. The endpiece has two orifices, one facing in the flow direction and the other in the opposite direction. Each of the orifices communicates via one of the concentric tubes with a different receptacle that is initially evacuated.

In that device, the sample taken is not representative of all of the flow inside the component in which the device is installed (film of liquid on the walls).

In addition, even if the sampling is said to be "isokinetic", there is nothing to guarantee that the flow speed of the sample taken is the same as that of the fluid flowing in the component. On the contrary, the technique of taking samples into evacuated receptacles inevitably leads to variations in pressure while the vessels are filling, and consequently to variations in sample speed as the samples are being taken.

Also, when the fluid sample has a very low liquid content, the necessary limited volume of the receptacles into which the samples are received has the consequence that the quantity of liquid taken is very small. Under such conditions, accurately measuring the ratio of liquid phase over gas phase is not possible. Similarly, it is not possible to envisage analyzing the nature of the liquid.

SUMMARY OF THE INVENTION

A specific object of the invention is to provide a method making it possible in genuinely isokinetic manner to take samples representative of a fluid such as that flowing in the gas outlet pipe of a liquid/gas separator.

According to the invention, there is provided a method of taking samples in the gas outlet pipe of a liquid/gas separator fed with an oil well effluent, comprising the steps of taking a sample continuously substantially from the center of said gas outlet pipe in the plane in which said pipe joins the separator, and regulating the sampling rate so that the velocities of the sample and of the flowing fluid are substantially the same.

In a preferred embodiment of the invention, the sample being taken is filtered continuously and the liquid it contains is collected for analysis and for volume measurement.

In a preferred embodiment of the invention, the flow rate $Qgsc$ of the gaseous fluid in the pipe is measured and the sampling rate is regulated to a determined value $Qsiso$ by applying a coefficient K to the measured flow rate $Qgsc$.

The coefficient K is determined using the following relationship:

$$K = 1 - \left(1 - \frac{d_i}{D_i}\right)^{(2n+1)/n} - \frac{2n+1}{n} \cdot \frac{d_i}{D_i}\left(1 - \frac{d_i}{D_i}\right)^{(n+1)/n}$$

where:
- $d_i$ represents the inside diameter (in meters) of a tube through which the sample is taken;
- $D_i$ represents the inside diameter (in meters) of the pipe; and
- n is an exponent, lying in the range 6 to 10 inclusive, depending on the flow profile of the fluid in the pipe.

In the above relationship, the exponent n is found by calculating the Reynolds number Re of the fluid flowing in the pipe, on the basis of the measured flow rate Qgsc, using the following relationship:

$$Re = 4 \frac{Q_{gsc} \cdot \rho_{gsc}}{\mu \cdot \pi \cdot D_i}$$

where:
- ρgsc represents the density of the fluid under standard conditions; and
- μ represents the dynamic viscosity (in Pa.s) of the fluid, under real conditions.

The invention also provides an apparatus for taking samples in the gas outlet pipe of a liquid/gas separator adapted to process oil well effluents, comprising a sampling tube opening out substantially on the axis of the pipe in a junction plane between the pipe and the separator and facing upstream in the fluid flow direction, and means for regulating the flow rate of the taken sample flowing continuously along the tube so that the velocities of the sample and of the fluid flowing in the pipe are substantially the same.

BRIEF DESCRIPTION OF THE DRAWINGS

A preferred embodiment of the invention is described below by way of non-limiting example and with reference to the accompanying drawing, in which:

FIG. 1 is a diagrammatic overall view of sample-taking apparatus of the invention installed on the gas outlet pipe of a liquid/gas separator forming part of a surface installation at an oil well; and FIG. 2 is a section in a plane perpendicular to that of FIG. 1 showing how the end of the sampling tube of the FIG. 1 apparatus is installed in the zone where the gas outlet pipe joins the separator receptacle.

DETAILED DESCRIPTION OF A PREFERRED EMBODIMENT OF THE INVENTION

In FIG. 1, reference 10 designates a liquid/gas separator receptacle forming part of a surface installation of an oil well under test. The petroleum fluid from the well penetrates into one end of the separator receptacle 10 via a horizontal inlet pipe 12. The petroleum fluid is caused to flow along the inlet pipe 12, and then through the separator receptacle 10 by the pressure that prevails at the downstream end of the well.

Inside the separator receptacle 10, the liquid and gas phases of the fluid are separated by gravity. More precisely, the major portion of the liquid phase L falls to the bottom of the separator receptacle 10 and is removed therefrom via a liquid outlet pipe 14. The gas phase G which occupies the upper portion of the separator receptacle 10 escapes therefrom via a gas outlet pipe 16. This gas outlet pipe 16 opens out into the separator receptacle 10 via an end portion that has its axis substantially vertical and that is connected to the top wall of the separator receptacle 10 in a plane that is substantially horizontal, as shown in FIGS. 1 and 2. Preferably, the end openings of the gas outlet pipe 16 and of the liquid outlet pipe 14 are placed close to an end of the separator receptacle 10 that is remote from the end opening of the inlet pipe 12. This conventional arrangement facilitates the flow of fluid from the inlet pipe 12 to the outlet pipes 14 and 16.

Inside the separator receptacle 10, the fluid pressure drops, thereby having the effect of forming microscopic liquid droplets. These droplets are not always trapped in the separator receptacle. On the contrary, because of the high flow rate of the fluid penetrating into the separator receptacle, a non-negligible fraction of the droplets is entrained into the gas outlet pipe 16.

The gas phase G which leaves the separator receptacle 10 via the gas outlet pipe 16 is thus constituted by a gaseous fluid containing liquid droplets in suspension.

In accordance with the invention, apparatus is provided for taking a sample representative of the gaseous fluid G in isokinetic manner from the gas outlet pipe 16. The isokinetic manner in which the sample is taken makes it possible to obtain precise information about the liquid fraction entrained in the gaseous fluid. The sampling apparatus also makes it possible to analyze separately the liquid entrained by the gaseous fluid and the gas phase proper. This information makes it possible to obtain accurate knowledge about the quantitative and qualitative characteristics of the fluid flowing in the well during testing.

In the special case of the fluid containing a very high gas content, knowledge of the liquid fraction entrained by the gas phase in the gas outlet pipe 16 makes it possible to measure accurately the liquid fraction contained in the fluid that penetrates into the separator receptacle 10. This measurement is obtained by adding to the liquid collected by the liquid outlet pipe 14 the liquid which is entrained by the gas phase via the gas outlet pipe 16.

As shown more precisely in FIG. 2, the sampling apparatus of the invention comprises a sampling tube 18 having an inlet portion placed coaxially inside the inlet portion of the gas outlet pipe 16 where it opens out into the separator receptacle 10. In the example described where the inlet portion of the gas outlet pipe 16 extends vertically, the inlet portion of the sampling tube 18 is therefore also vertical. In addition, the inlet portion of the tube 18 faces downwards, i.e. into the separator receptacle 10, and it lies substantially in the plane where the pipe 16 joins the wall of the receptacle.

This particular arrangement ensures that a sample can be taken continuously that is as representative as possible of the gaseous fluid leaving the separator receptacle 10 via the gas outlet pipe 16.

Downstream from its inlet position, the sampling tube 18 passes in sealed manner through the wall of the gas outlet pipe 16, as shown diagrammatically in the form of a plug 20 in FIG. 1.

In its portion situated outside the gas outlet pipe 16, the sampling tube 18 passes successively through a first filter 22, a second filter 24, a flow meter 26, and a regulator valve 28. Beyond the regulator valve 28, the sampling tube 18 may either open out to the atmosphere, as shown diagrammatically at 18a, or else it may open out into the gas outlet pipe 16 downstream from the sampling point and the main regulator valve 43, as shown diagrammatically at 18b.

The sampling apparatus also comprises lagging 30 surrounding the sampling tube 18 over its portion situated outside the gas outlet pipe 16, at least as far as the filters 22 and 24. As shown in FIG. 1, the lagging 30 preferably surrounds the sampling tube 18 to beyond the regulation valve 28.

Finally, the sampling apparatus of the invention comprises a regulator 32 and a second flow meter 34 placed in the gas outlet pipe 16. It should be observed that the flow meter 34 is a device that is normally to be found in existing surface installations.

As shown diagrammatically by dashed lines in FIG. 1, the flow meters 26 and, preferably, 34 are electrically connected to the regulator 32. In this way, the electrical signals delivered by the flow meters 26 and 34 and representative of the flow rates respectively in the sampling tube 18 and in the gas outlet pipe 16, are applied continuously to the regulator 32 when the apparatus is in operation. On the basis of these flow rate signals, the regulator 32 establishes a signal for correcting the flow rate in the sampling tube 18. This flow rate correction signal is applied to the regulator valve 28 via a connection that is likewise represented by dashed lines in FIG. 1.

As described in greater detail below, the flow correction signal makes it possible to maintain the flow rate of the gaseous fluid sample flowing continuously along the sampling tube 18 at a value such that the speed of the sample and the speed of the gaseous fluid flowing in the gas outlet pipe 16 are permanently substantially the same. It is thus ensured that sampling is isokinetic. The flow meters 26 and 34, the regulator 32, and the regulator valve 28 constitute means for regulating the flow rate in the sampling tube 18.

The flow meters 26 and 34 are preferably mass flow meters and generally identical to those normally fitted to surface installations of oil wells. They deliver signals that are representative of mass flow rates under standard conditions. The flow rate value measured by the flow meter 26 is written Qsmes and the flow rate value measured by the flow meter 34 s written Qgsc.

The regulator 32 is preferably a triple-action or PID regulator, i.e. it is a proportional, integral, and differential regulator.

On the basis of the flow rate values Qsmes and Qgsc applied thereto by the flow meters 26 and 34, the regulator 32 determines the correction that needs to be applied to the flow rate in the sampling tube 18 for the speed of the sample taken by said tube to be substantially equal to the speed of the gaseous fluid flowing along the gas outlet pipe 16. To this end, the regulator 32 compares the flow rate value Qsmes as measured by the flow meter 26 with a target value to be achieved Qsiso, which is established from the value Qgsc measured by the flow meter 32 in the pipe 16. Depending on the difference that exists between the values Qsmes and Qsiso, the regulator 32 acts on the regulator valve 28 so as to cancel this difference continuously.

The flow rate Qsiso to be established in the sampling tube 18 is calculated in the regulator 32 by applying the relationship:

$$Qsiso = K \cdot Qgsc \quad (1)$$

in which K represents a coefficient which depends on the ratio of the sections of the sampling tube 18 and of the gas outlet pipe 16 and on the speed profile in the pipe. This coefficient is given by the following relationship:

$$K = 1 - \left(1 - \frac{d_i}{D_i}\right)^{(2n+1)/n} - \frac{2n+1}{n} \cdot \frac{d_i}{D_i}\left(1 - \frac{d_i}{D_i}\right)^{(n+1)/n} \quad (2)$$

in which:
  $d_i$ represents the inside diameter (in meters) of the sampling tube 18;
  $D_i$ represents the inside diameter (in meters) of the gas outlet pipe 16; and
  n represents an exponent which depends on the flow profile of the gaseous fluid in the pipe 16.

More precisely, the regulator 32 determines the value of the exponent n in the range 6 to 10 inclusive after calculating the Reynolds number Re of the gaseous fluid flowing in the gas outlet pipe 16.

The relationship between the exponent n and the Reynolds number Re is fixed in conventional manner by an empirical relationship. Thus, the exponent n is given the value 6 when the Reynolds number Re lies in the range $10^3$ to $5.7 \times 10^4$, the value 7 when the Reynolds Re lies in the range $5.7 \times 10^4$ to $6 \times 10^5$, the value 8.8 when the Reynolds number Re lies in the range $6 \times 10^5$ and $2.2 \times 10^6$, and finally the value 10 when the Reynolds number Re lies in the range $2.2 \times 10^6$ and $10^7$.

To calculate the Reynolds number, the regulator 32 uses the following relationship:

$$Re = 4\frac{Q_{gsc} \cdot \rho_{gsc}}{\mu \cdot \pi \cdot D_i} \quad (3)$$

in which:
  $\rho gsc$ represents the density of the gaseous fluid flowing in the pipe 16 under standard conditions; and
  $\mu$ represents the dynamic viscosity (in Pa.s) of the fluid under real conditions.

The density values $\rho gsc$ are determined previously, either by a corresponding measurement, or by calculation when the components of the fluid are known. In comparable manner, the values for the dynamic viscosity $\mu$ are determined either by correlation or by calculation.

If the measurements actually performed do not enable relationship (3) to be applied directly, e.g. because of an offset that exists between standard conditions and measurement conditions, then application of this relationship can be preceded by calculating the mean speed of the gaseous fluid in the gas outlet pipe 16. Pressure and temperature are then measured in the pipe by appropriate measurement means (not shown).

The sample which is thus taken at a regulated flow rate via the sampling tube 18 arrives first at the first filter 22. This filter 22 has a filter cartridge which collects the liquid in suspension in the gaseous fluid. The collected liquid flows into a receptacle 36 where its volume is measured. A system of valves 38 makes it possible to cause the receptacle 36 to communicate with a container (not shown) for transporting the liquid sample. The container may convey all of the liquid, or only a fraction thereof, to an analysis laboratory in which the various physical and chemical characteristics of the liquid entrained by the gas phase in the pipe 16 are determined.

Periodically changing the filter cartridge of the first filter 32 ensures that it continues to operate at maximum effectiveness.

The second filter 24 is identical to the first filter 22. Its function is essentially to confirm that the first filter is effective. Thus, the appearance of liquid in the second filter leads to the filter cartridge of the first filter 22 being replaced immediately.

Downstream from the filters 22 and 24, a branch connection 40 is generally provided on the sampling tube 18. This branch 40 makes it possible to collect a sample of gas that does not contain liquid, e.g. in a tank 42. The tank can also be transferred to an analysis laboratory where the physical and chemical characteristics of the gas are determined.

The lagging 30 enables the sample taken by the tube 18 to be maintained at its sampling temperature, at least until the liquid it contains has been trapped by the filter 22. This prevents a portion of the liquid condensing on the wall of the sampling tube 18, thus ensuring that all of the liquid entrained by the gaseous fluid is indeed collected in the first filter 22.

We claim:

1. A method of taking samples in the gas outlet pipe of a liquid/gas separator fed with an oil well effluent, comprising the steps of taking a sample continuously substantially from the center of said gas outlet pipe in the plane in which said pipe joins the separator, and regulating the sampling rate so that the speeds of the sample and of the flowing fluid are substantially the same.

2. A method according to claim 1, in which the sample is filtered continuously and the liquid it contains is collected.

3. A method according to claim 2, in which the collected liquid is analyzed and its volume is measured.

4. A method according to claim 2 or 3, in which a fraction of the sample is collected after being filtered.

5. A method according to claim 1, in which the sample is discarded.

6. A method according to claim 1, in which the sample is recycled into said pipe downstream from the point at which it was taken.

7. A method according to claim 1, in which the flow rate Qgsc of the fluid in the pipe is measured and the sampling flow rate is regulated to a determined value Qsiso by applying a coefficient K to the measured flow rate Qgsc.

8. A method according to claim 7, in which the coefficient K is determined from the relationship:

$$K = 1 - \left(1 - \frac{d_i}{D_i}\right)^{(2n+1)/n} - \frac{2n+1}{n} \cdot \frac{d_i}{D_i}\left(1 - \frac{d_i}{D_i}\right)^{(n+1)/n}$$

in which:
di represents the inside diameter (in meters) of a tube via which the sample is taken;
Di represents the inside diameter (in meters) of said gas outlet pipe; and
n represents an exponent, lying in the range 6 to 10 inclusive, depending on the flow profile of the fluid in the pipe.

9. A method according to claim 8, in which the exponent n in the above relationship is selected by calculating the Reynolds number Re of the fluid flowing in the pipe, on the basis of the measured flow rate Qgsc, and using the relationship:

$$Re = 4\frac{Q_{gsc} \cdot \rho_{gsc}}{\mu \cdot \pi \cdot D_i}$$

in which:

ρgsc represents the density of the fluid under standard conditions; and $\mu$ represents the dynamic viscosity (in Pa.s) of the fluid, under real conditions.

10. Apparatus for taking samples in the gas outlet pipe of a liquid/gas separator adapted to process oil well effluents, comprising a sampling tube opening out substantially on the axis of the pipe in a junction plane between the pipe and the separator and facing upstream in the fluid flow direction, and means for regulating the flow rate of the taken sample flowing continuously along the tube so that the speeds of the sample and of the fluid flowing in the pipe are substantially the same.

11. Apparatus according to claim 10, in which filter means are placed in the sampling tube to collect the liquid contained in the sample.

12. Apparatus according to claim 11, in which the filter means comprise two filters connected in series, and a liquid receptacle communicating with at least the first of the filters.

13. Apparatus according to claim 12, in which a container for transporting the liquid of the sample is adapted for connection to the receptacle via a normally closed valve.

14. Apparatus according to claim 10, in which lagging surrounds the sampling tube at least as far as and including the filter means.

15. Apparatus according to claim 10, in which means are provided for taking a sample of gas from the sampling tube downstream from the filter means.

16. Apparatus according to claim 10, in which the means for regulating the flow rate comprise:
a first flow meter placed in the pipe;
a second flow meter placed in sampling tube;
a regulator valve placed in the sampling tube; and
a regulator responsive to signals delivered by the first and second flow meters to control the regulator valve.

* * * * *